United States Patent [19]

Greenberg et al.

[11] Patent Number: 5,128,245
[45] Date of Patent: Jul. 7, 1992

[54] ESTABLISHMENT, CHARACTERIZATION AND DIFFERENTIATION OF A NEW MEGAKARYOCYTIC CELL LINE, THE DAMI CELLS

[75] Inventors: Sheryl M. Greenberg, Brighton; Robert I. Handin, Needham, both of Mass.

[73] Assignee: Brigham and Women's Hospital, Boston, Mass.

[21] Appl. No.: 232,987

[22] Filed: Aug. 17, 1988

[51] Int. Cl.$^5$ .............. C12Q 1/02; C12P 21/00; C12N 5/00; C12N 5/02

[52] U.S. Cl. .................. 435/29; 435/70.1; 435/70.3; 435/70.4; 435/240.1; 435/240.2; 435/240.25

[58] Field of Search .......... 435/240.1, 240.2, 29, 435/68.1, 70.1, 70.3, 70.4, 2, 13, 240.25; 436/503, 63, 87

[56] References Cited

U.S. PATENT DOCUMENTS

4,710,381 12/1987 Kunicki et al. ............... 424/101

FOREIGN PATENT DOCUMENTS

2079292 1/1982 United Kingdom .

OTHER PUBLICATIONS

S. M. Greenberg et al., *Blood* 70 (*Supp 1*): 154a, Abstract No. 470 (1987)
S. M. Greenberg-Sepersky et al., *Thromb. Res.* 24:299–306 (1981).
M. Ogura et al., *Blood* 66:1384–1392 (1985).
D. Seigneurin et al., *Exp. Hematol.* 15:822–832 (1987).
P. Martin et al., *Science* 216:1233–1235 (1982).
A. Tabilio et al., *EMBO J* 3:453–459 (1984).
R. Michalevicz et al., *Leuk. Res.* 9:441–448 (1985).
G. W. Sledge et al., *Cancer Res.* 46:2155–2159 (1986).
J. Loscalzo et al., *Biochem.* 23:3880–3886 (1984).
D. D. Wagner et al., *J. Cell Biol.* 99:2123–2130 (1984).
S. M. Greenberg et al., *J. Biol. Chem.* 262:3269–3277 (1987).
Greenberg et al. (ARI), "Development and Characterization of a new megakaryocytic cell line: The Dami Cell", Blood 70(5) 1987.
Greenberg et al., "Characterization of a New Megakaryocytic Cell Line: The Dami Cell", Blood, vol. 72(6), 1968–1977, Dec.–88.
Morgan et al. (AT3), "Novel peripheral blood derived human cell lines with properties of megakaryocytes", J. Cell Biology, vol. 100, 565–573, 1985.
Kieffer et al., "Expression of Platelet Glycoprotein Ibα in HEL cells", J. Biological Chemistry, vol. 261, 15854–15862, 1986.
Kellar et al., "Thrombopoietin stimulation of megakaryocytopoiesis in Agar Culture", Megakaryocyte Development and Function, pp. 209–213, 1986.

*Primary Examiner*—Elizabeth C. Weimar
*Assistant Examiner*—Gail Poulos
*Attorney, Agent, or Firm*—Sterne, Kessler, Goldstein & Fox

[57] ABSTRACT

A stable mutant human megakaryocytic cell line is disclosed which is useful for the study of megakaryocytopoiesis, platelet formation and production, platelet component formation, and the identification and characterization of factors which modulate megakaryocytopoiesis.

5 Claims, 11 Drawing Sheets

ESTABLISHMENT, CHARACTERIZATION AND DIFFERENTIATION OF A NEW MEGAKARYOCYTIC CELL LINE, THE DAMI CELLS

The research underlying this patent application was supported by National Institutes of Health Grants P01 HL 33014 and R01 HL 34787; the Government has certain rights in this invention.

FIELD OF THE INVENTION

The invention relates to a new mutant cell line. Specifically, the invention relates to a human megakaryocytic cell line which is useful for the identification and study of megakaryocytopoiesis and platelet formation and platelet component formation and the factors which modulate megakaryocytopoiesis.

BACKGROUND OF THE INVENTION

Platelets, and the components which they secrete upon activation, play a major role in hemostasis, thrombosis and the development of atherosclerosis (see Petersdorf, R. G., et al., eds., *Principles of Internal Medicine*, 10th edition, 1983, McGraw-Hill, New York, pp. 292–294 and 1468). Megakaryocytes in the bone marrow form platelets by pinching off pieces of their cytoplasm.

Upon injury to a tissue, blood platelets adhere to the exposed subendothelial tissue through adhesive platelet components. These components also promote platelet-platelet interactions and smooth muscle cell proliferation in response to platelet-derived growth factors. Platelets adhere to other membranes through their membrane protein GPIb to von Willebrand factor (a component of clotting factor VIII) in the subendothelial matrix. This is followed by platelet clot formation by interactions between GPIIb/IIIa, as well as von Willebrand factor, platelet factor 4 and fibrinogen which are secreted from the platelet alpha granules into the interstitial spaces of the clot. Thus, the efficacy of platelet participation in normal processes, as well as in atherosclerosis, is largely dependent upon adequate numbers of platelets and adequate concentrations of the participating components in the platelet membranes and granules.

Platelet production is controlled by sequential regulation of the component steps of megakaryocytopoiesis: 1) commitment of pluripotent stem cells to the megakaryocyte lineage, 2) proliferation of the committed stem cells, 3) cytoplasmic maturation, 4) polyploidization, and 5) platelet release. Greenberg-Sepersky, S. M., et al., *Thrombo. Res.* 24:299–306 (1981). However, the process of platelet production which occurs at the level of differentiation and maturation of the parent megakaryocytes in the bone marrow is poorly understood.

To date, several humoral factors have been postulated to regulate the steps of megakaryocytopoiesis in vivo and in vitro. In colony-forming assays, which measure the proliferation of committed stem cells, megakaryocyte colony-stimulating factor (Meg-CSF), megakaryocyte potentiator (MK-POT), interleukin-3 (IL-3), interleukin-1 (IL-1), erythropoietin (EPO), and granulocyte-macrophage colony-stimulating factor (GM-CSF), all increase the number and size of megakaryocyte colonies in vitro. Thrombocytopenic serum, a source of the uncharacterized factor "thrombopoietin," or the conditioned medium from bone marrow cultures and cultured human embryonic kidney cells increases the number, ploidy, and size of megakaryocytes in vitro, and the incorporation of radiolabelled precursors into the membrane and alpha granules of newly-released platelets in vivo.

A major limitation of most of these studies is the lack of a purified megakaryocytic cell system. All of the studies which examine megakaryocyte differentiation utilize bone marrow cell preparations. However, except for studies which utilize primary cultures of a single bone marrow cell type, interpretation of the results is complicated by the presence of non-megakaryocytic cells which may act as accessory cells.

The mechanisms controlling thrombopoiesis are not well understood due to the inability to isolate megakaryoblasts away from other bone marrow cells in the absence of accessory cells, and due to the unavailability of a cultured cell line which can serve as a model of the differentiating megakaryocyte. Megakaryocyte differentiation and maturation is characterized by increased polyploidization and enhanced expression of platelet membrane proteins such as GPIb, GPIIb/IIIa and platelet-specific alpha granule formation.

Cell lines which display the characteristics of megakaryocytic cell have been reported. However, these cell lines are limited in their ability to be used as models of megakaryocyte differentiation. For example, MEG-01 cells have been reported to be a megakaryoblastic cell line. However, MEG-01 cells contain the important platelet marker antigen, GPIb, only in the cytoplasm of a subpopulation of larger MEG-01 cells rather than uniformly expressing it on the surface of all the cells. Ogura, M., et al., *Blood* 66:1384–1392 (1985).

LAMA-84 cells are a megakaryocytic cell line which expresses the platelet marker proteins GPIIb/IIIa. However, LAMA-84 cells do not express the platelet marker protein GPIb. In addition, the LAMA cell line is not committed to the megakaryocytic lineage, but rather represents an earlier stage in differentiation as shown by the fact that they are a tripotent, megakaryocytic, erythroid, and granulocytic cell line. Seigneurin, D., et al., *Exp. Hematol.* 15:822–832 (1987).

The mutant human megakaryocytic cell line, the HEL cell, does not express the beta subunit for GPIb platelet marker protein and contains an abnormally glycosylated alpha subunit for GPIb. Kieffer, et al., *J. Biol. Chem.* 261:15854–15862 (1986); Martin et al., *Science* 233-1235 (1982); Tabilio, A., et al. *EMBO J.* 3:453–459 (1984).

A promyelocytic leukemic cell line, HL60, responds to inducers of platelet synthesis such as 12-0-tetradecanoyl phorbol 2-acetate (TPA). However, HL60 cells respond to TPA by differentiating to either monocytes or granulocytes instead of inducing platelet production. Michalevicz, R., et al., *Leuk. Res.* 9:441–448 (1985).

Morgan, D. A., et al., *J. Cell. Biol.* 100:565–573 (1985) reported a series of human cell lines with properties of megakaryocytes which were isolated and cultured from peripheral blood. However, none of these cell lines are capable of differentiating to a cell with the characteristics of platelet late differentiation morphology, such as alpha granule formation.

The megakaryocytic cell line EST-IU expresses the platelet marker proteins GP IIb/IIIa on its membrane. Sledge, G. W., et al., *Cancer Res.* 46:2155–2159 (1986). However, this cell line routinely dies after six months of continuous cell culture (30–35 cell divisions).

Thus, there remains a need for a purified megakaryocytic cell population, in which the culture conditions can be carefully manipulated and the results easily monitored, to study the process of megakaryocytopoiesis, to evaluate the effects of megakaryocytopoietic, hemopoietic and nonhemopoietic factors on the megakaryocyte system, to study platelet formation and release from the parent megakaryocyte (thrombopoiesis), to provide a source for the purification of megakaryocyte and platelet components, to identify new megakaryopoiesis factors from crude preparations and to serve as an assay system for the subsequent isolation and characterization of those new factors.

SUMMARY OF THE INVENTION

The present invention provides a continuous and permanently established human megakaryocytic cell line, originally derived from the blood of a patient with megakaryoblastic leukemia, and mutants thereof, demonstrated by its ability to be propagated continuously using routine cell culture techniques, and by having the following characteristics:

(a) a doubling time of 24-30 hours;

(b) uniform expression of platelet membrane glycoproteins GPIb and GPIIb/IIIa on the cell membrane of about 90% of the cell population;

(c) the ability to synthesize and secrete von Willebrand factor and thrombospondin;

(d) the ability to respond to phorbol 13-myristate 12-acetate by increasing expression of GPIb, GPIIb/IIIa, GMP-140, von Willebrand factor and thrombospondin, and by more than 40% of the cells increasing their ploidy levels, from 2N and 4N, to 8N, 16N, 32N, 64 N and 128N;

(e) the ability to differentiate along the platelet linage in response to interleukin-3 and thrombopoietic stimulatory factors by increasing synthesis of platelet alpha granule proteins including thrombospondin, and von Willebrand factor;

(f) a negative reaction with anti-BI antibodies;

(g) a negative reaction with anti-TI or anti-TII antibodies;

(h) a negative reaction with anti-Mol antibodies.

The present invention also provides a cell line which can be used in experiments which require homogeneous cultures of megakaryocytes for the study of megakaryocytopoiesis and thrombopoiesis.

The invention further provides a cell line which provides a source for the purification and characterization of megakaryocyte and platelet components.

The present invention provides a cell line which can be used for the study of the mode of action of hormones and other factors implicated in the regulation of megakaryocytopoiesis and thrombopoiesis, and for the identification, isolation, and characterization of factors which regulate megakaryocytopoiesis and thrombopoiesis.

BRIEF DESCRIPTION OF THE DRAWINGS

FIGS. 1(A) and 1(B) Wright-Giemsa-stained smear prepared from the patient's blood obtained at the same time the Dami cells cultures were initiated. FIG. 1A: Blast cells with irregular nuclei, budding cytoplasm, megakaryocytic fragments; FIGS. 1B: A large polyploid megakaryoblast with budding cytoplasm, and a large megakaryocytic fragment. A nucleated red blood cell is also noted. (original magnification $\times 630$).

FIG. 3) Wright-Giemsa-stained preparations of cultured Dami cells. FIG. 3B Cell smears prepared after one year of continuous culture. (original magnification $\times 630$).

FIG. 6) Flow cytometric analysis of propidium iodide-stained nuclei. Exponentially growing Dami cells were solubilized with a Nonidet P-40-containing buffer and the nuclei stained with propidium iodide. Freshly prepared lymphocytes were used as 2N standards. Five thousand cells were analyzed for each sample. The first major peak is representative of the proportion of cells in the population with a normal 2 N complement of DNA. The subsequent peaks represent the proportion of cells with ploidies of 4N, 8N, 16N, 32N, and greater levels of DNA shown on a log scale of the DNA content.

FIG. 6A: Untreated cells; FIG. 6B: cells treated with PMA and cultured for 4 days; FIG. 6C: Cells treated with PMA and cultured for 10 days.

FIGS. 10(A) and 10(B) Von Willebrand factor analysis.

DETAILED DESCRIPTION OF THE INVENTION

The invention provides an immortal line of human megakaryocytic cells. These cells are capable of mitotically proliferating and continuously growing in suitable culture medium and environmental conditions. Additionally, these cells uniformly express marker proteins found in megakaryocytes in vivo. Additionally, these cells are capable of responding in vitro to factors known to regulate megakaryocytopoiesis in vivo. Additionally, these cells are capable of serving as a source for the purification of megakaryocyte and platelet components. Additionally, these cells are capable of serving as a model system to assay for the presence of factors which modulate megakaryocytopoiesis in crude and purified preparations of these factors. A deposit of the megakaryocytic cell line has been made with the American Type Culture Collection, 12301 Parklawn Drive, Rockville, Md. 20852, USA, on Aug. 12, 1988, and is assigned the accession number ATCC CRL 9792.

The present invention relates to a permanently established human megakaryocytic cell line which was isolated and purified from the blood of a 57 year old man suffering from megakaryoblastic leukemia. These cells, which are herein designated "Dami" cells and which have been in continuous culture for over 19 months, provide rapidly growing cultures of a pure megakaryocytic cell line which has the following characteristics:

(a) Form: The Dami cells uniformly express the megakaryocyte phenotype as demonstrated by the synthesis of GpIb, GpIIb/IIIa, von Willebrand factor and thrombospondin. Cells are 12–120 microns in diameter and contain lobulated nuclei and a few alpha granules; the cells have a doubling time of 24–30 hr during exponential growth;

(b) Proliferation: The Dami cells proliferate satisfactorily in phytohemagglutinin-stimulated leukocyte conditioned medium and Iscove's Modified Dulbecco's Medium containing 10% horse serum;

(c) Subculture: The Dami cells can be subcultured continuously and indefinitely;

(d) Preservation: The Dami cells can be preserved in liquid nitrogen for a prolonged period of time and for at least 18 months;

(e) Ploidy levels: Fewer than 10% of exponentially growing Dami cells have DNA ploidy levels greater than 4N. In response to the tumor-promoting phorbol ester, phorbol 12-myristate 13-acetate (PMA, also abbreviated as TPA), over 40% of the cells achieve ploidy levels greater than 4N, with the highest ploidy levels between 64N and 128N. This polyploidization is unique to cells of the megakaryocyte linage in normal bone marrow, and only occurs during megakaryocyte differentiation and development;

(f) Expression of platelet marker proteins: The Dami cells uniformly express platelet glycoproteins Ib (GPIb) and GPIIb/IIIa on the surface of all the cells; The cells express both chains of GpIb;

(g) Immunoreactivity: The Dami cells do not react with anti-B1 antibodies, which are reactive with immature and mature B cells; anti-T1 or anti-T11 antibodies, which are reactive with immature and mature T cells; nor with anti-Mo1 antibodies, which are reactive with myeloid cells throughout maturation;

(h) Response to Interleukin 3 and thrombopoietic stimulatory factors (TSF): The Dami cells increase synthesis of platelet alpha granule proteins, thrombospondin and von Willebrand factor;

(i) Response to the phorbol esters: In response to the tumor promoting phorbol ester, PMA, the Dami cells increase the number of GPIb and GPIIb/IIIa molecules on the cell's plasma membrane; the cells become more polyploid so that as many as 40% of the cells have ploidy levels of 8N, 16N, 32N, 64N, and 128N; the amount of von Willebrand factor and thrombospondin secreted per cell is increased.

Examples of reagents which can be used to examine megakaryocyte differentiation and platelet formation in Dami cell cultures include: DMSO; PMA; sources of hemopoietic factors such as ITP serum; aplastic anemia serum, thrombocytopenic serum, and plasma and bone marrow-conditioned medium; purified hemopoietic factors, such as erythropoietin, GMCSF and GCSF; and, lymphokines such as, interleukin-3, and interleukin-1. As known by those of skill in the art, a range of concentrations of these factors or a combination of these factors can be used to study the response of the Dami cells.

By megakaryocytic or platelet component is meant any substance synthesized by the megakaryocyte or platelet.

By response of the Dami cells is meant a change in any measurable parameter which is the result of the presence of a factor or other stimulus. The response may be a morphological response, for example, a change in the size of the cell or a ploidy level; or it may be a biochemical response such as a change in the level of a metabolite, protein, lipid, carbohydrate, nucleic acid or other macromolecule, especially macromolecules which are regulated by alterations in the rate of their transcription, translation, post-translational processing, secretion or degradation.

Mutants of this cell line can be generated by any appropriate mutagenesis method, for example, by irradiation, infection, transfection, or chemical mutation and that mutants can be screened by assaying the appearance, disappearance or altered expression of particular platelet cell components, such as von Willebrand factor, thrombospondin, GPIb or any appropriate parameter.

Megakaryocyte or platelet components can be prepared from the cell lysate or supernatant fraction of the cell culture by any appropriate separation technique or combination of techniques appropriate for the component being extracted such as chromatography, electrophoresis, or centrifugation including high pressure liquid chromatography, ion-exchange chromatography, adsorption chromatography, paper chromatography, gel chromatography, affinity chromatography including immunoaffinity chromatography, hydrophobic interaction chromatography, covalent chromatography, hydroxyapatite chromatography, thin layer chromatography, gas-liquid chromatography, gel electrophoresis including polyacrylamide or agarose gels, or combinations thereof, sodium dodecyl sulfate gel electrophoresis, moving boundary electrophoresis, zone electrophoresis, paper electrophoresis, cellulose acetate strip electrophoresis, gradient electrophoresis, isoelectric focusing, immunoelectrophoresis, ultracentrifugation, isokinetic or linear gradient centrifugation, zonal centrifugation, cesium chloride centrifugation, polyethyleneglycol fractionation and precipitation, salt fractionation and precipitation, or membrane filtration. Using the above-described techniques, one can prepare megakaryocytic or platelet components from the cell line of the present invention such as thrombospondin, GPIb, von Willebrand factor, etc. In a preferred embodiment, the above-described techniques are especially useful in the preparation of von Willebrand factor. Von Willebrand factor has been isolated previously from other sources, for example, U.S. Pat. No. 4,710,381, Great Britain Patent Application Publication No. 2,079,292 and in Loscalzo, J., et al., *Biochem.* 23:3880–3886 (1984) and Wagner, D. D., et al., *J. Cell. Biol.* 99:2123–2130 (1984).

Having now generally described this invention, the same will be better understood by reference to certain examples which are included herein for purposes of illustration only and are not intended to be limiting unless otherwise specified.

EXAMPLE 1

Isolation of the Dami Cell Line

Case History. The cell line was derived from the peripheral blood of a 57 year old male with megakaryoblastic leukemia. The patient was originally diagnosed as having myeloid metaplasia with myelofibrosis in 1975. In 1983, he was treated with hydroxyurea because of progressive splenic enlargement and weight loss. Two years later he developed left upper quadrant pain and fever, and underwent splenectomy. The spleen weighed 5,041 grams and had extensive extramedullary hematopoiesis with myeloid, erythroid, and megakaryocytic elements. Following splenectomy, his platelet count rose to 1,830,000/μL and white blood cell count to 110,000/μL with megakaryocytic fragments and megakaryoblasts identified in the blood. Over the next 24 months he received several courses of chemotherapy which included various combinations of cytosine arabinoside and Daunarubicin but failed to enter hematologic remission. Blood was taken for cell analysis and a heparinized blood sample was obtained, with the patient's consent, in December, 1986, for the initiation of cell culture. The patient died the next month, 13 years after initial diagnosis and 1 year after conversion to acute megakaryocytic leukemia.

Figure 1A:
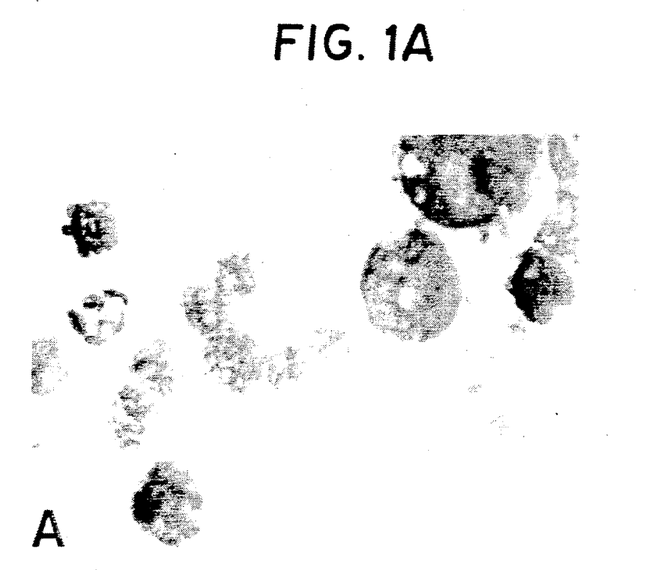
Figure 1B:
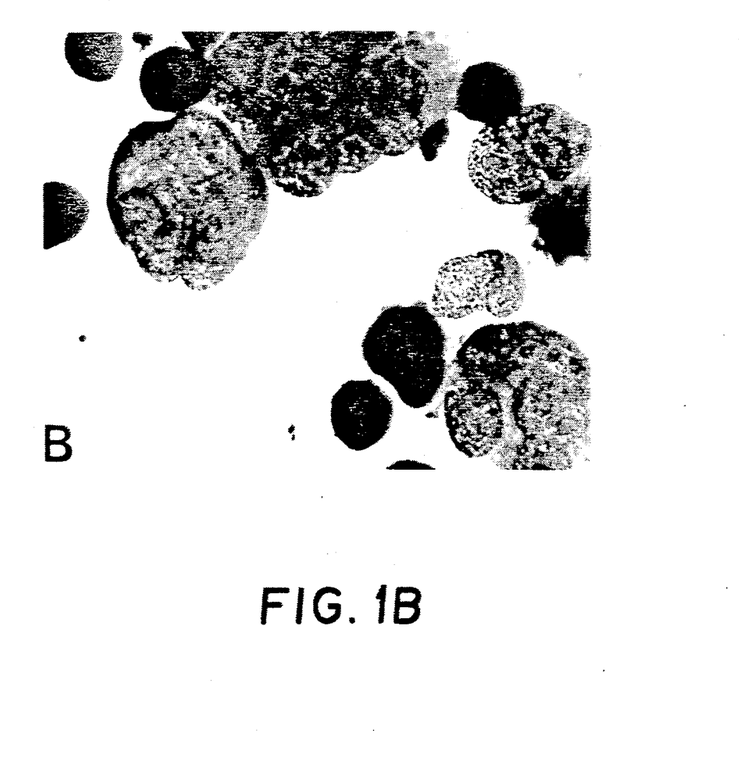

Morphologic Examination. At the time the megakaryoblastic cells were isolated from the patient's blood, his white cell count was 54,000/μL (corrected for nucleated red blood cells), with 63% megakaryoblasts and the platelet count was 21,000/μL. The differential count revealed 2% neutrophils, 20% lymphocytes, 1% monocytes, 2% basophils, 6% myelocytes, 5% promyelocytes, and 61% blast forms. In addition, there were 27 nucleated red blood cells and 37 megakaryocytic fragments per 100 white cells. Wright-Giemsa staining of blood smears, FIG. 1 (A and B), demonstrated the high percentage of blasts. The immature cells had irregular nuclei and budding cytoplasm. Large platelet forms, megakaryocyte fragments, nucleated red cells and polyploid megakaryoblasts were also noted.

The blood samples were diluted four-fold with Hank's Balanced Salt Solution (HBSS), and fractionated on discontinuous two-step Percoll (Pharmacia Fine Chemicals, Piscataway, N.J.) gradients with densities of 1.050 and 1.085 gm/cc. Greenberg, S. M., et al., *J. Biol. Chem* 262:3269 (1987). The cells harvested from the interface between the two layers of Percoll were washed twice in HBSS and suspended in 10% horse serum in Iscove's Modified Dulbecco's Medium (IMDM) (GIBCO Laboratories, Grand Island, N.Y.) containing 1% phytohemagglutininstimulated leukocyte-conditioned medium (PHA-LCM) in plastic tissue culture flasks. The cell were subcultured as necessary. No feeder cells were used.

EXAMPLE 2

Cell Culture and Growth Characteristics

Figure 2:
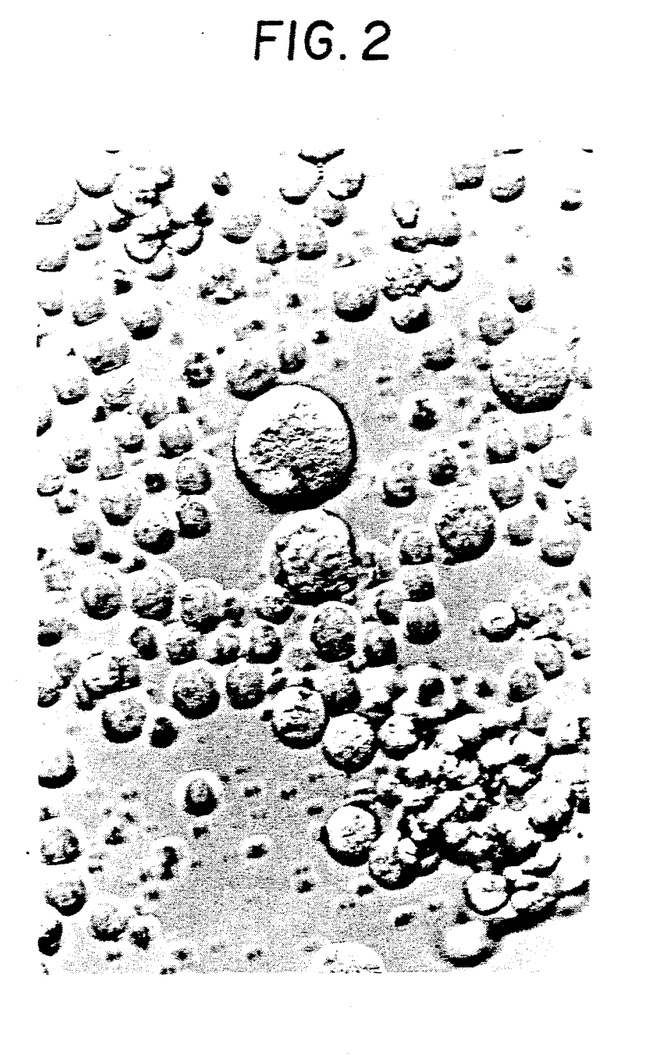
FIG. 2) Phase photomicrograph of Dami cells in culture. Confluent Dami cells were photomicrographed through an inverted microscope with phase contrast illumination after eight months in culture. (original magnification $\times 400$).

The Dami cells proliferated very slowly for the first few weeks after initiation of culture, but began to proliferate rapidly after week twelve, with a doubling time of 24–30 hours. Typically, the cells require subculturing twice-weekly. The Dami cells adhere to tissue culture plasticware until the cell density begins to increase, after which they grow as both adherent cells, and in grape-like clusters in suspension (FIG. 2). Numerous large round refractile cells were seen growing in suspension as well as adherent to the culture dish. There was a large variability in cell size with a range of 12–120 microns in diameter. Also notable were multilobed nuclei in the larger cells. Typically, even the adherent cells were rounded, although, cytoplasmic protrusions or pseudopods were often observed in viable cells. Greater than 95% of the cells excluded trypan blue and were thus considered viable; the nonviable cells were usually rounded and/or fragmented. The Dami cells have maintained a population doubling time of 24–30 hours during exponential growth and have been maintained in continuous culture for 19 months. Culture in the presence of $5\times10^{-9}$M PMA results in substantial decrease in proliferation, increased adherence to tissue culture plasticware, and increased cell spreading. They are free from Epstein Barr virus.

EXAMPLE 3

Long Term Morphologic Examination

Figure 3A:
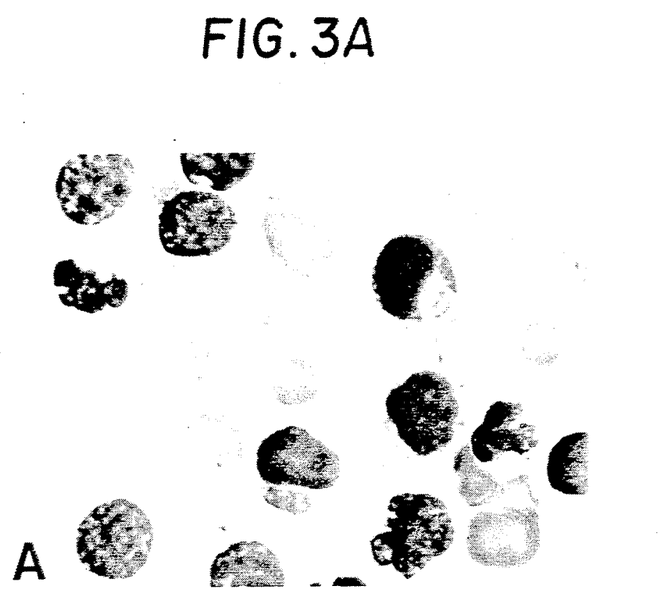
FIG. 3A: Cytospun cells prepared three months after the initial isolation and culture of the Dami cell line, stored frozen, and stained with Wright-Giemsa.
Figure 3B:
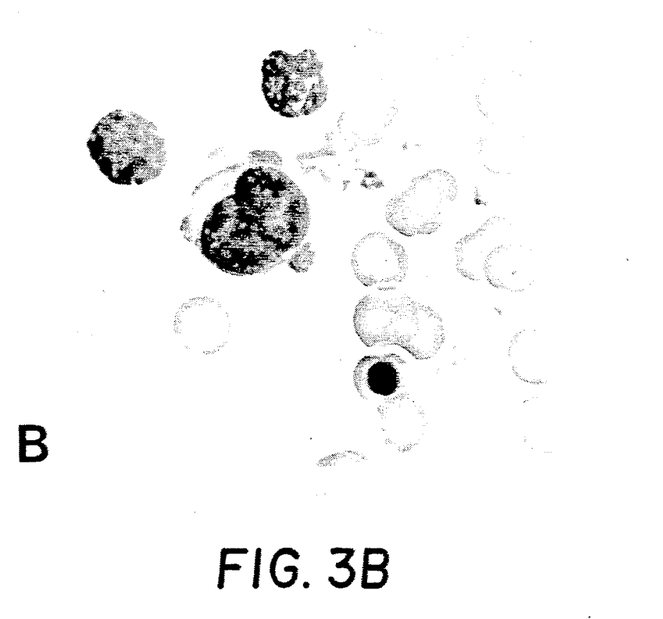

The cultured Dami cells were examined periodically. Cells obtained at 12 weeks, shortly after the cells began proliferating, were frozen and compared to smears of cells maintained in continuous culture for one year (FIG. 3 (A and B)). In samples compared after three months of continuous culture, many polyploid immature cells are noted. In smears prepared after one year of continuous culture, the findings are similiar and reveal polyploid blast cells with frequent budding of the cytoplasm, as well as smaller, less differentiated blast cells. In each case, the cytoplasm was basophilic and devoid of granules.

EXAMPLE 4

Ultrastructural Studies

Dami cells were harvested for ultrastructural studies after six months of continuous culture. Cells were centrifuged at $400\times g$ for 5 minutes, and washed with phosphate-buffered saline (PBS) prior to preparation of electron microscopy studies essentially according to the method of Schmit, A. et al., *Carbohydr. Res.* 151:173 (1986). Briefly, the cells were fixed in 2.5% glutaraldehyde in 0.1M cacodylate buffer (pH 7.2) at ambient temperature for one hour, and postfixed in 1% osmium tetroxide containing 1% potassium ferricyanide, dehydrated with ethanol and propylene oxide, and embedded in Epon. Thin sections of selected areas were stained with uranyl acetate followed by lead citrate, and examined with Philips EM 300 electron microscope.

Figure 4:
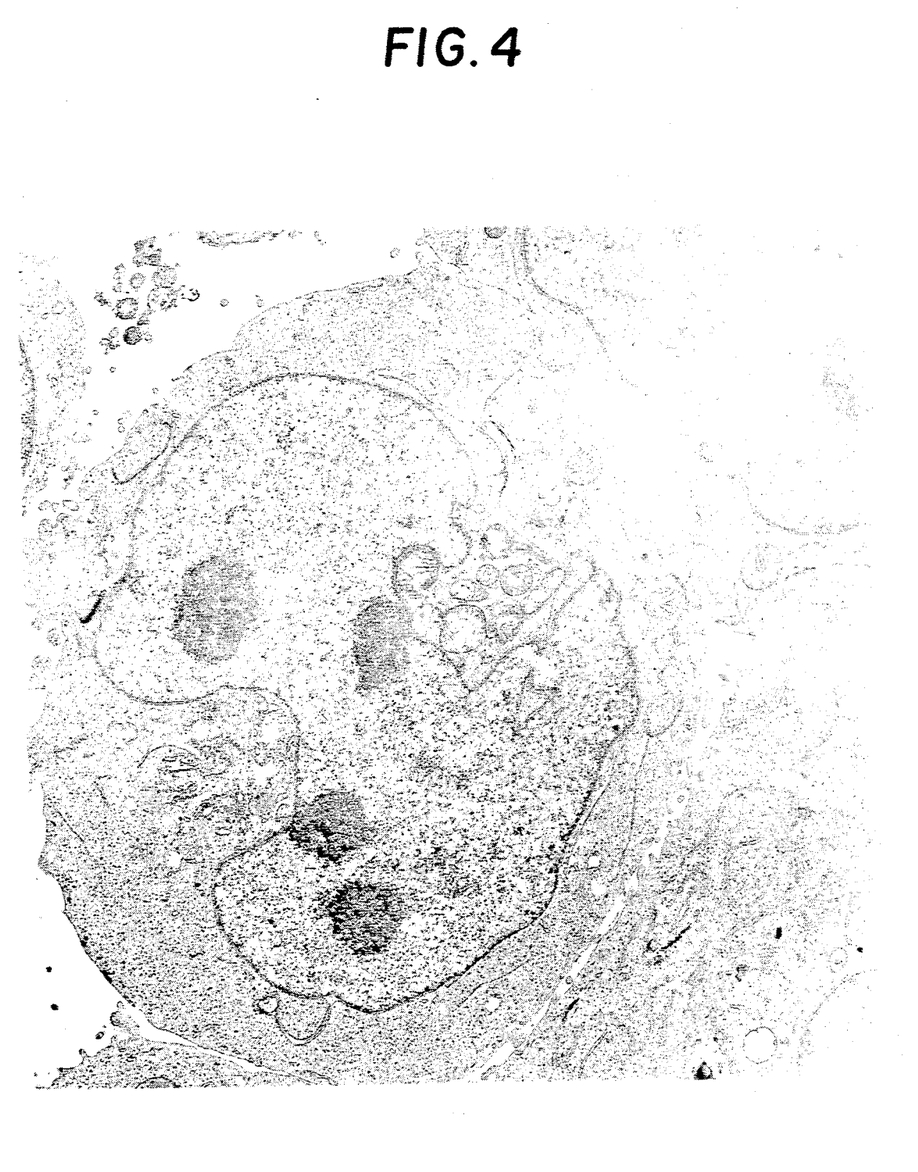
FIG. 4) Transmission electron micrograph of Dami cells after eight months in culture. (original magnification $\times 9555$).

The Dami cell population so examined was heterogenous with cells having characteristics of megakaryoblasts or immature megakaryocytes. Multiple prominent nucleoli were present in a lobulated nucleus. The cytoplasm contained prominent smooth endoplasmic reticulum, extensive Golgi complex, numerous enlarged mitochondria; no granules or demarcation membranes were noted. The predominant cell contained a lobulated nucleus, multiple, prominent nucleoli and a high nuclearcytoplasm volume ratio (FIG. 4). The cytoplasm contained prominent smooth endoplasmic reticulum, extensive Golgi complex, and numerous large mitochondria. Only rare granules were seen. Cytoplasmic budding was frequently observed but no demarcation membranes were noted.

EXAMPLE 5

Cytogenetic Analysis

Exponentially growing cells were exposed to colcemid (0.1 μg/mL) (GIBCO Laboratories, Grand Island, N.Y.) for 30 minutes, and washed by centrifugation. The cell pellet was resuspended in a hypotonic solution of 75 mM KCI, for 10 minutes at ambient temperature, centrifuged, and fixed in freshly-prepared methanol:glacial acetic acid (3:1 v/v) which was changed twice. Aliquots of the cell suspension were dropped onto cold wet sides and allowed to air dry.

Slides were Q-banded by staining in an aqueous solution of quinacrine mustard (Sigma Chemical Company) using published protocols. Tantravahi, R., et al., *Cancer Genet. Cytogenet.* 30:83 (1983). Thirty well-spread and banded metaphases were photographed using a Leitz fluorescence microscope equipped with an Orthomat camera. Chromosome analysis was done from photographic prints. The chromosome abnormalities are described according to the International Society for Cytogenetic Nomenclature in Harden, D. G., et al. *An International System for Human Cytogenetic Nomenclature,* Karper, Basil (1985).

Figure 5:
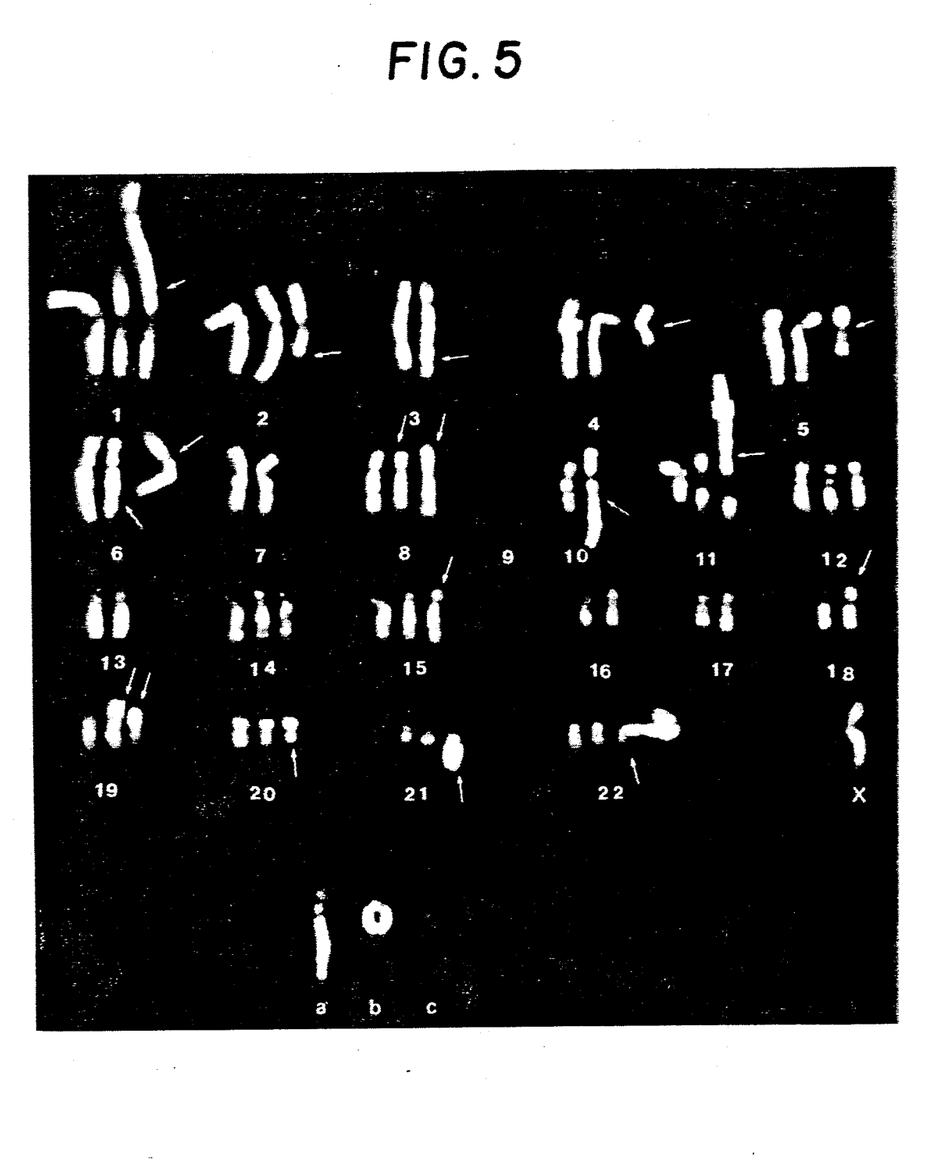
FIG. 5) A representative karyotype of the Dami cell line from a metaphase stained for Q-1 bands. Arrows point to the structural rearrangements observed as clonal abnormalities: a) a 5;6 translocation, b) ring chromosome, c) pale staining fragment.

Cytogenetic studies of peripheral blood and a bone marrow aspirate taken in 1983, when the patient presented with splenic enlargement, revealed a normal 46,XY karyotype. This cell line, the Dami cells, was established from a peripheral blood sample obtained in 1986, and, after eight months in culture, the Dami cell line had a near triploid chromosome number with a range of 54–64 chromosomes. Several clonal structural abnormalities were observed in the twenty cells analyzed (FIG. 5). Chromosomal aberrations of the major clone are summarized in Table 1. There were trisomies of sixteen of the autosomal chromosomes. There were also deletions of specific regions on chromosomes 4, 6 and 20. A large number of reciprocal translocations were identified. The four completely defined translocations involve chromosomes 1 and 6, 3 and 6, 4 and 8, and 5 and 17. A majority of the cells had a normal X and Y chromosome.

TABLE 1

| Cytogenetic Analysis of Dami Cells After Eight Months in Continuous Culture | |
|---|---|
| Chromosome number | 54–64 XY |
| Trisomies | +1,+2,+3,+4,+5,+6,+8,+11, +12,+13,+15,+17,+19,+20,+21, +22 |
| Deletions | 4(q25),6(q21),20(q12) |
| Completely-defined Translocations | t(1;6) (p13;p21) |
| | t(3;6) (p13;q16) |
| | t(4;8) (q12;p11) |

TABLE 1-continued

| Cytogenetic Analysis of Dami Cells After Eight Months in Continuous Culture | |
|---|---|
| | t(5;17) (q11;p11) |
| Partially-defined Translocations | t(1;?) (p21;??) |
| | t(2;1)) (10;?) (q21;p14,q23:??) |
| | t(3;?) (q26;??) |
| | t(8;?) (p11;??) |
| | t(9;?;11) (p24;??;p15) |
| | t(9;?;22) (p24;??;p13) |
| | t(15;?) (p11;??) |
| | t(18;?) 9p11;??) |
| | t(19;?) (p11;??) |
| | t(19;?) (p13;??) |

EXAMPLE 6

Ploidy Analysis

Control and PMA-treated cells were cultured for 4 days. The cells were then washed twice with HBSS and suspended in nuclei isolation medium (NIM), a calcium- and magnesium-free HBSS containing 0.2% bovine serum albumin, 0.4% Nonidet P-40 and 10 mM HEPES, pH 7.4 at a concentration of $2 \times 10^6$/mL. RNase (54 Worthington Units/mL), and an equal volume of NIM buffer containing 25 μg/mL propidium iodide, were added. The suspensions were placed in an ice bath for at least 30 minutes prior to flow cytometric analysis on a Becton Dickinson Flow Cytometry Analyzer equipped with the appropriate excitation (long pass: 400 nm, band pass: 485/20 nm) and emission (band pass: 575/26, long pass: 570 nm) filters. The ploidy distribution of the cells was compared to freshly prepared lymphocytes and to propidium iodide 2N standard beads (Flow Cytometry Standards Corp., Research Triangle Park, N.C.).

Figure 6A:
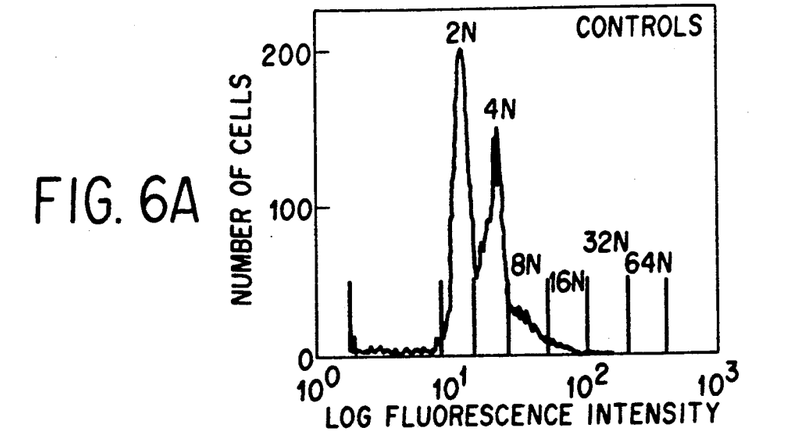
Figure 6B:
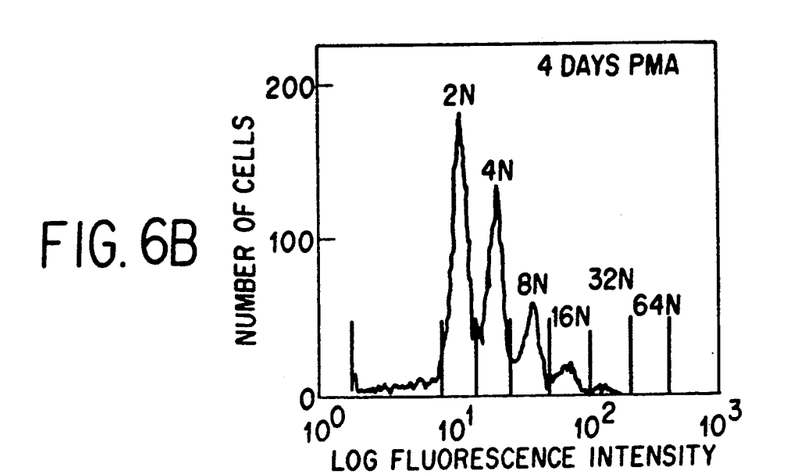
Figure 6C:
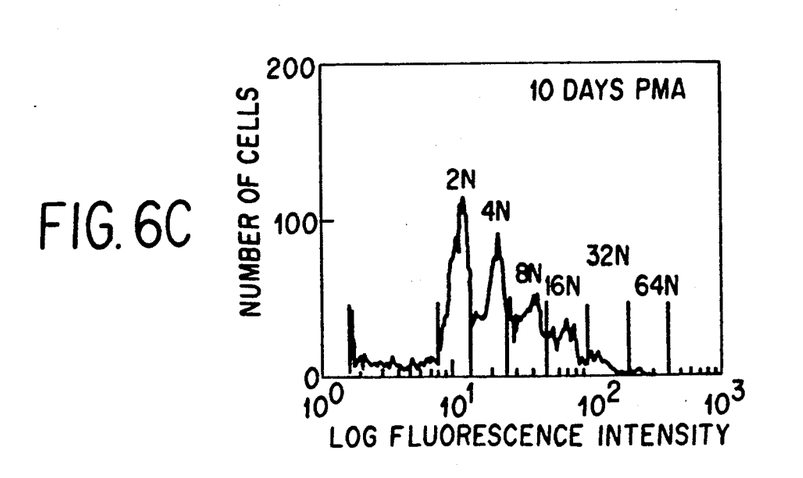
Figure 7A:
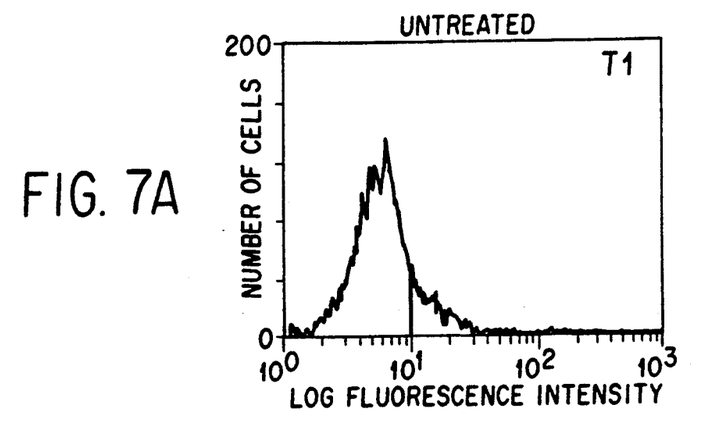
FIG. 7) Indirect immunofluorescence flow cytometric analysis of cultured Dami cells. The top panel represents cells reacted with anti-T1, a pan T cell monoclonal antibody, as negative controls and plotted on a log scale of fluorescence intensity. The two lower panels represent cells reactive with 6D1 and 10ES, monoclonal antibodies against platelet glycoproteins Ib and IIb/IIIa, respectively. The left panels represent control cells cultured in the absence of any inducing reagents; the right panels represents cells cultured in the presence of PMA. Five thousand cells were analyzed for each sample.
Figure 7B:
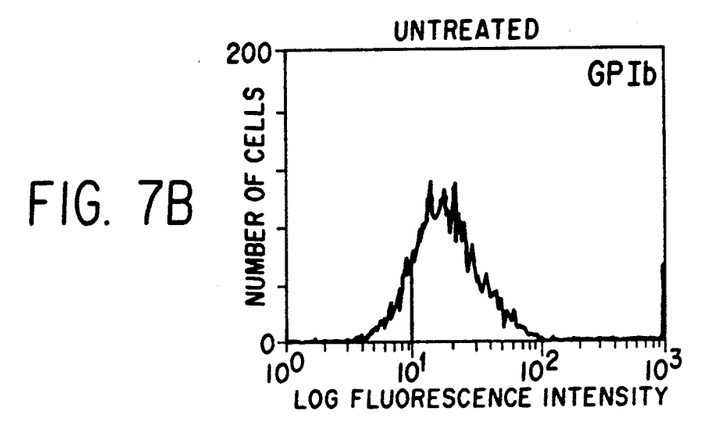
Figure 7C:
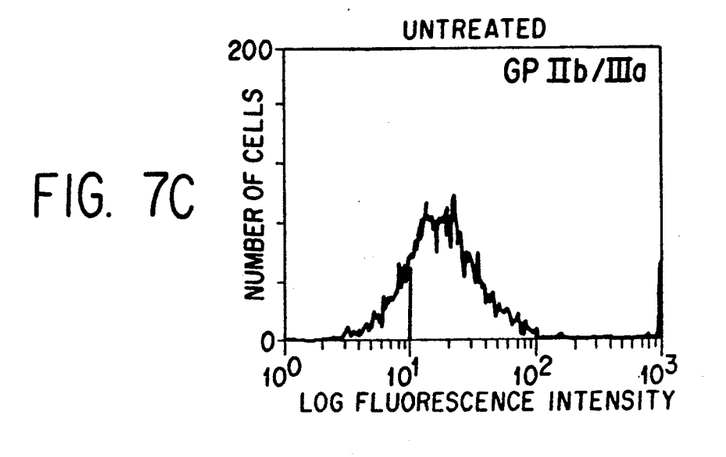
Figure 7D:
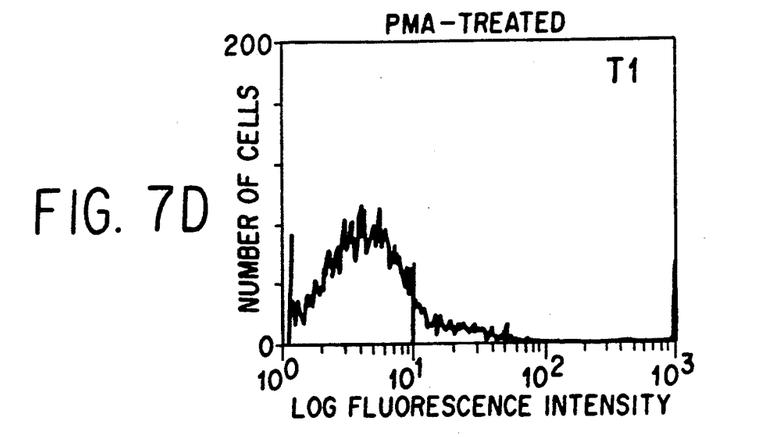
Figure 7E:
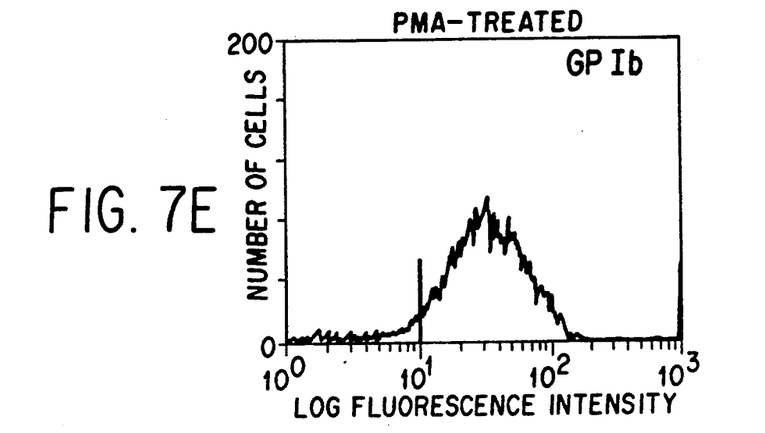
Figure 7F:
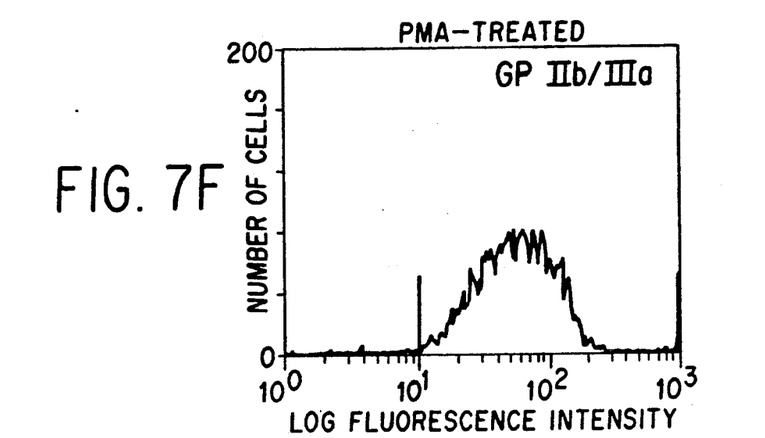

Nuclei isolated from exponentially growing Dami cells (5000 from each sample) were predominantly 2N and 4N (45.0% and 38.0%, respectivelly) with a small proportion (12.8%) containing DNA equivalents of 8N or greater (FIG. 6). These results are consistent with normal megakaryocytes where a small percent of the cell population spontaneously achieves ploidy levels greater than 4N. When viewed by a fluorescence microscope, these polyploid nuclei did not appear to be aggregates of isolated nuclei.

To confirm the ploidy distribution measured by using isolated nuclei, as well as to demonstrate that the polyploid nuclei were not merely aggregates, another method was used which utilizes intact cells treated with hypotonic citrate to facilitate nuclear staining by propidium iodide, Fried, J. et al. *J. Cell Biol.* 71:172 (1976). The ploidy distribution was confirmed, and no cell aggregates were detected by fluorescence microscopy. Cultures treated with the tumor-promoting phorbol ester, PMA, for either 4 or 10 days, had a greater proportion of cells containing complements of DNA greater than 4N (22.7% and 36.7%) than control cells suggesting maturation of the cells. In addition, these polyploid Dami cells fell neatly into distinct groups containing 8N, 16N, 32N, and 64N levels of DNA. DMSO (1.25%) had a negligible effect on the Dami cell ploidy levels. Other hematopoietic cell lines, including HEL, K562, U937 and HL-60 cells, did not increase the ploidy distribution of the cells when incubated with PMA.

EXAMPLE 7

Cell Surface Markers

The expression of surface antigens was analyzed by using a panel of monoclonal antibodies recognizing epitopes on hematopoietic cells. Cultured cells were washed in HBSS, adjusted to a concentration of $1 \times 10^6$/ml, and incubated for 30 minutes at 4° C. with equivalent protein concentrations (2 µg/$10^6$ cells) of monoclonal antibodies against platelet GPIb, antibody 6DI, Coller, B. S., et al., *Blood* 61:99 (1983)); and the GPIIb/IIIa complex, antibodies 7E3, Coller, B. S., *J. Clin. Invest.* 76:101 (1985), and 10E5, Coller, B. S., et al., *J. Clin. Invest.* 72:325 (1982)); glycophorin A, Barnstable, C., et al., *Cell* 14:9 (1978); HLA class I antigen, antibody W6/32, Cannistra, S. A. et al., *J. Clin. Invest.* 77:13 (1986); or monoclonal antibodies against T cells, (anti-T1, Reinberz, E. L., et al., *Cell* 30:735 (1982), and anti-T11, Kamoun, M., et al., *J. Exp. Med.* 153:207 (1981)); B cells, (anti-B1, Nadler, L. M., et al., *J. Clin. Invest.* 67:134 (1981)); myeloid and monocytic cells, antibody My9, Griffin, J. D., et al., *Leuk. Res.* 8:521 (1984); Koike, T., et al., *Blood* 69:957 (1987)); or monocytic/macrophagic/granulocytic cells, antibody Mo1, Todd, RF III, et al., *Blood* 59.775(1982)), purchased from Coulter Immunology, Hialeah, Fla. Mouse IgG or IgM was used for the determination of negative or background staining. After two washes by centrifugation in HBSS, the cells were incubated with the FITC-conjugated goat anti-mouse IgG or IgM at a dilution of 1:100 for 30 minutes at 4° C. After an additional centrifugation in PBS containing 1% paraformaldehyde, the number of cells reactive with each antibody was analyzed by flow cytometry on a Becton Dickinson Flow Cytometry Analyzer equipped with the appropriate excitation (long pass:400 nm. band pass:485/20 nm) and emission (band pass 530 nm) filters. At least 5000 cells were analyzed for each antibody, and the experiment was conducted every 3 months after cell proliferation began (12 weeks after the initial seeding of the patients fractionated blood). The proportion of "positive" cells was determined by comparison to cells reacted with nonspecific mouse IgG or IgM, or with the FITC-conjugated secondary antibody alone, as negative control.

The results of cell surface antigen analysis are summarized in Table 2. Nearly all of the cultured cells expressed platelet glycoproteins Ib and IIb/IIIa, as well as glycophorin. HLA class I antigen, and the myeloid antigen recognized by the My9 antibody. Less than 10% of the cells reacted with the FITC-conjugated secondary antibody alone, and were referenced as negative staining. Lymphoid antigens were uniformly absent, as were those of monocytes, granulocytes, and macrophages.

Indirect immunofluorescence histograms of control and PMA-treated cultured Dami cells demonstrated an increased surface expression of the platelet glycoproteins Ib and the IIb/IIIa complex in response to PMA (FIG. 7). Non-specific antibody binding did not increase, concomitantly, as shown by the similar fluorescence distributions of control or PMA-treated cells reacted with anti-T1, an antibody against a T cell antigen present throughout T cell maturation (FIGS. 7A and 7D); cell reactivity with the secondary, fluorescently-tagged antibody alone was similar to that with anti-T1.

TABLE 2

| Surface Antigen Characterization of the Dami Cells | | |
|---|---|---|
| Monoclonal Antibody | % Positive Cells* | Antibody Specificity |
| 6DI | 95.7 | Platelet GPIB |
| 7E3 | 94.7 | Platelet GPIIb/IIIa |
| 10E5 | 93.4 | Platelet GPIIb/IIIa |
| B1 | negative | immature and mature B cells |
| T1 | negative | immature and mature T cells |
| T11 | negative | immature and mature T cells |
| Mo1 | negative | pan myeloid cells |
| My9 | 84.1 | multipotent progenitors |
| W6/32 | 95.0 | HLA class I antigen |
| Glycophorin A | 88.6 | Glycophorin A |

*"Negative" denotes <10% positive cells. Values represent the averages of the three separate determinations.

EXAMPLE 8

SDS-Polyacrylamide Gel Electrophoresis and Western Blot Analysis

Cells were removed from the culture dishes with 10 mM EDTA, lysed in the presence of 0.5% Nonidet P-40, 10 mM TES, pH 7.4, 0.15M NaCl, mM EDTA, 2 mM phenylmethylsulfonyl fluoride (PMSF), 50 µg/mL leupeptin, and 3 mM iodoacetamide, and applied to SDS-polyacrylamide gels (SDS-PAGE) for electrophoresis. SDS-PAGE was carried out employing the discontinuous system of Laemmli, U. K., *Nature* 227:680 (1970), using 5–15% linear polyarylamide gradients. The proteins were electrophoretically transferred to nitrocellulose as previously described, Greenberg, S. M., et al.. *J. Biol. Chem.* 262:3269 (1987), and the nitrocellulose blots were stained with rabbit polyclonal antibodies prepared against GPIb and von Willebrand factor. Affinity-purified goat anti-rabbit IgG radiolabelled with $^{125}$I was incubated with the nitrocellulose filters for one hour at ambient temperature. The filters were washed with Tris-buffered saline containing 0.05% Tween-20 and exposed to XAR film (Kodak Laboratories) for autoradiography.

Figure 8:
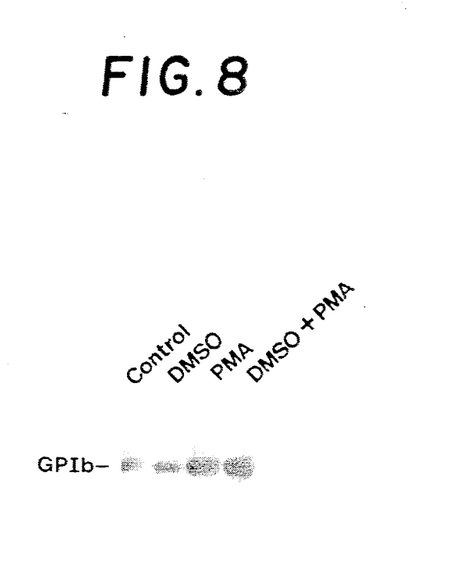
FIG. 8) SDS-PAGE and Western blot analysis of GPIb. Lysates of $2.5 \times 10^5$ control and DMSO-and/or PMA-induced Dami cells were electrophoresed in each lane of an SDS-PAGE gel, and subsequently transferred electrophoretically to nitrocellulose filters. The nitrocellulose filters were stained with rabbit polyclonal antibodies against platelet GPIb, and then with an $^{125}$I-labeled, affinity purified, goat anti rabbit IgG.

Electrophoresis of control, DMSO- and PMA-stimulated Dami cell lysates, and the lysates of cells stimulated with both reagents, in SDS-polyacrylamide gels demonstrated that the Dami cells express a normal-sized platelet GPIb of 170 kD (FIG. 8) which when reduced, decreases in size to 140 kD, the same size as a platelet GPIbα chain (FIG. 8). This suggests that the Dami cells also express the GPIbβ chain, which is translated from a different messenger RNA than that which encodes the GPIbα chain. PMA stimulation increases the number of molecules of GPIb per cell when equivalent numbers of cells are electrophoresed (FIG. 8), confirming the increased reactivity with the monoclonal antibody against GPIb demonstrated in FIG. 7.

EXAMPLE 9

Northern Blot Analysis

Total RNA was prepared from $5 \times 10^7$ cells by guanidine hydrochloride extraction, and electrophoresed in 1% agarose denaturing gels as previously described, Doi, T. D., et al., *Mol. Cell. Biol.* 7:898 (1987). Equal amounts of total RNA (10 mg) from each sample were electrophoresed and then transferred electrophoretically to Zetaprobe filters (BioRad Laboratories). A cDNA probe of GPIb was radiolabelled using the method of random hexanucleotide priming and used for hybridization. Filters were washed at high stringency (0.1×SSC, 0.1% SDS, 55° C.) and exposed to XAR film for autoradiography.

Figure 9:
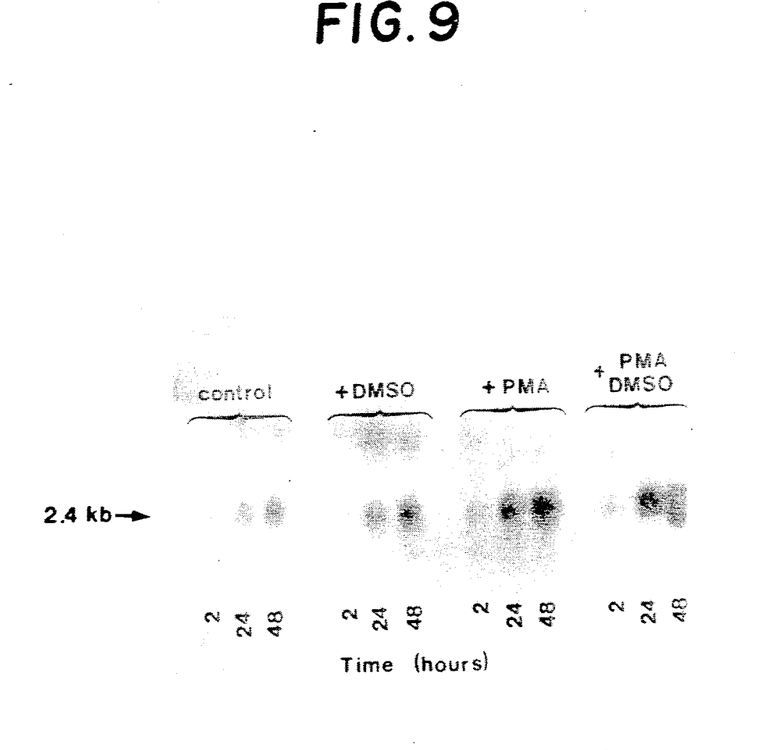
FIG. 9) Northern blot analysis of Dami cell RNA. Ten micrograms of total RNA prepared from control, DMSO- and/or PMA-induced Dami cells at 2, 24 and 48 hours after the initiation of culture and addition of inducing reagents, were electrophoresed in 1% agarose formaldehyde gels, and electroblotted onto Zetaprobe filters. The filters were hybridized with a $^{32}$P-labeled cDNA probe of GPIb, washed at high stringency, and autoradiographed.

Hybridization of Northern blot filters with radiolabelled cDNA probes revealed the presence of the 2.4 kb mRNA for GPIbα in Dami cells (FIG. 9). Comparison of equivalent amounts of total RNA from control, DMSO- and PMA-stimulated cells, as well as RNA from cells stimulated by both reagents, demonstrates that PMA, but not DMSO, enhances the expression of GPIb mRNA and that the increased surface expression of GPIb is due, at least in part, to an increase in the level of the GPIb specific mRNA. The level of expression is maximal at least 48 hours after the cells are subcultured, or after PMA is added.

EXAMPLE 10

Analysis of von Willebrand factor

For quantitative measurement of von Willebrand factor antigen in the conditioned medium, Dami cells were cultured with 1% Nutridoma-HU (Boehringer-Mannheim), and in the absence of exogenous von Willebrand factor sources such as horse serum and phytohemagglutinin-stimulated leukocyte conditioned medium. Quantitation of von Willebrand factor was preformed by inhibition ELISA.

Figure 10A:
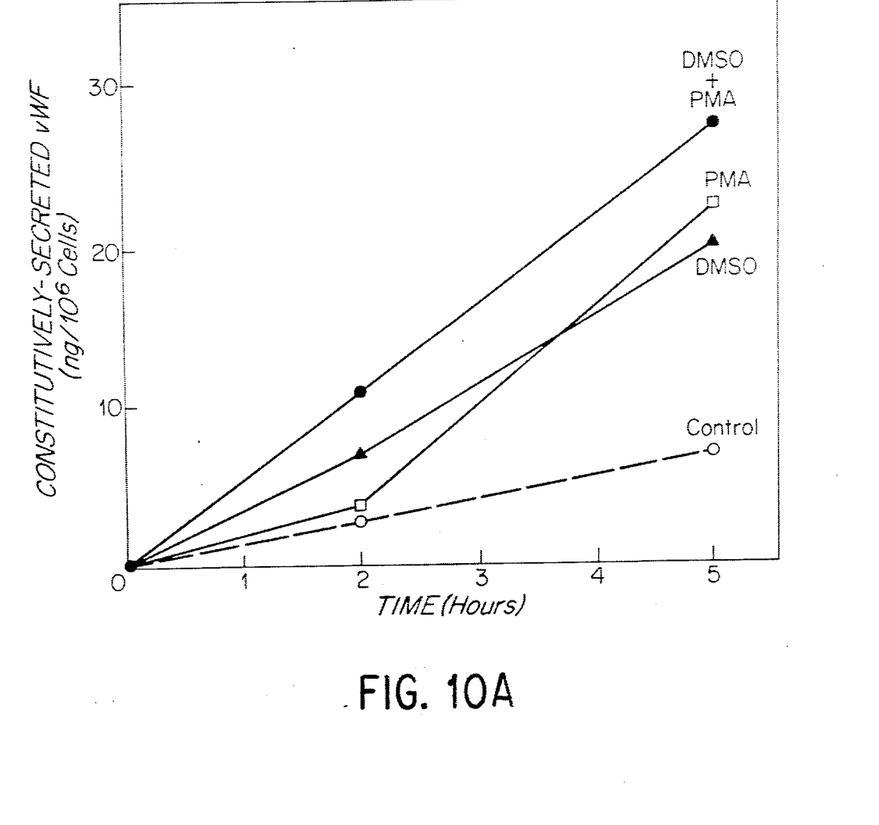
FIG. 10a: Conditioned medium of Dami cultured for 0, 2 and 5 hours in the absence of exogenous sources of von Willebrand factor and in the presence of PMA and/or DMSO where indicated, were assayed by inhibition ELISA.
Figure 10B:
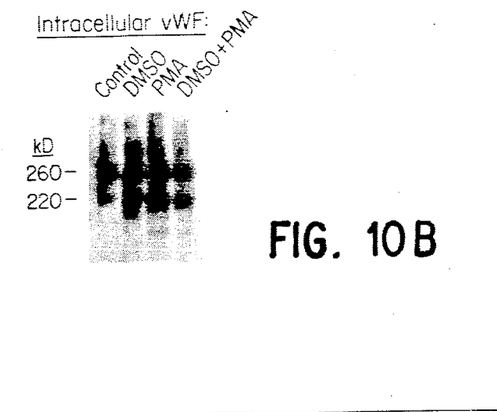
FIG. 10B: Western blot analysis of intracellular von Willebrand factor in lysates of $2.5 \times 10^5$ Dami cells after culture in the presence of PMA and/or DMSO as indicated. Nitrocellulose filters were stained with polyclonal rabbit anti-von Willebrand factor antiserum and $^{125}$I-labeled, affinity-purified goat anti-rabbit IgG, and autoradiographed.

Dami cells washed free of and cultured in the absence of exogenous sources of von Willebrand factor but in the presence of PMA and/or DMSO constitutively secrete von Willebrand factor antigen. Quantitation of secreted von Willebrand factor by inhibition ELISA demonstrated that both, PMA and/or DMSO, increase the amount of secreted antigen about three-fold (FIG. 10A). Western blot analysis of lysates from control and stimulated cell demonstrated the presence of the intracellular precursor forms of von Willebrand factor (260 and 275 kD) as well as the fully processed (220 kD) form of von Willebrand factor. The pattern is identical to that seen in endothelial cells and normal guinea pig megakaryocytes (30,31). In contract to GPIb, which is only enhanced by PMA, the addition of either PMA or DMSO, enhanced von Willebrand factor expression (FIG. 10B).

Now having fully described this invention, it will be understood by those with skill in the art that the scope may be performed within a wide and equivalent range of conditions, parameters, and the like, without affecting the spirit or scope of the invention or of any embodiment thereof.

What is claimed is:

1. A continuous and permanently established human megakaryocytic cell line, originally derived from the blood of a patient with megakaryoblastic leukemia, and having the following characteristics:
   (a) a doubling time of 24–30 hours;
   (b) uniform expression of platelet membrane glycoproteins GPIb and GPIIb/IIa on the cell membrane of about 90% of the population;
   (c) the ability to synthesize and secrete von Willebrand's factor and thrombospondin;
   (d) the ability to respond to phorbol 13-myristate 12-acetate by increasing expression of GPIb, GPIIb/IIIa, GMP-140, von Willebrand factor and thrombospondin, and by more than 40% of the cells increasing their ploidy levels, from 2N and 4N, to 8N, 16N, 32N, 64N and 128N;
   (e) the ability to differentiate along the platelet linage in response to interleukin-3 and thrombopoietic stimulatory factors by increasing synthesis of platelet alpha granule proteins including thrombospondin and von Willebrand factor;
   (f) a negative reaction with anti-B1 antibodies;
   (g) a negative reaction with anti-T1 or anti-T11 antibodies;
   (h) a negative reaction with anti-Mo1 antibodies;
   (i) a negative reaction for Epstein Barr virus;
   (j) expression of the beta subunit of GpIb; and
   (i) expression of GpIb of a molecular weight identical to the molecular weight of GpIb normally found in platelets; and wherein said cell line is the cell line ATCC No. CRL 9792.

2. A process for assaying a megakaryocytic regulatory factor comprising incubating in a suitable culture medium the human cell line as defined in claim 1 and the megakaryocytic regulatory factor-containing sample, and monitoring the response of said cells to the sample.

3. The process of claim 2, wherein the megakaryocytic regulatory factor is thrombopoietin.

4. A process for preparing a megakaryocytic or platelet component comprising incubating in a suitable culture medium the human cell line as defined in claim 1 and separating the component from the cell lysate or supernatant fraction of the culture.

5. The process of claim 4, wherein said component is von Willebrand factor.

* * * * *